United States Patent
Bär et al.

(10) Patent No.: US 6,471,819 B1
(45) Date of Patent: Oct. 29, 2002

(54) METHOD AND DEVICE FOR COATING A SURFACE WITH A PLASTIC FILM

(75) Inventors: Kai K. O. Bär, Bruckmühl-Heufeld (DE); Rainer Gaus, Bruckmühler-Heufeld (DE)

(73) Assignee: Advanced Photonics Technologies AG, Bruckmuhl-Heufeld (DE)

( * ) Notice: Subject to any disclaimer, the term of this patent is extended or adjusted under 35 U.S.C. 154(b) by 0 days.

(21) Appl. No.: 09/647,408

(22) PCT Filed: Mar. 30, 1999

(86) PCT No.: PCT/EP99/02173
§ 371 (c)(1),
(2), (4) Date: Sep. 29, 2000

(87) PCT Pub. No.: WO99/50048
PCT Pub. Date: Oct. 7, 1999

(30) Foreign Application Priority Data

Mar. 31, 1998 (DE) ............................. 198 14 390

(51) Int. Cl.[7] .................... B32B 31/26; B31F 5/00; B05C 11/00; B24C 71/04; H01K 1/28
(52) U.S. Cl. ................. 156/272.2; 156/273.3; 156/379; 156/379.6; 156/379.8; 156/499; 118/713; 118/620; 118/642; 427/508; 427/542; 427/557; 313/113
(58) Field of Search ................ 156/272.2, 273.3, 156/311, 230, 236, 379, 379.6, 379.8, 391, 499; 427/487, 508, 542, 555, 557; 313/113; 118/713, 620, 642

(56) References Cited

U.S. PATENT DOCUMENTS 4,900,583 A * 2/1990 Hirabayashi et al. ......... 427/55
6,068,722 A * 5/2000 Yu et al. ....................... 156/137

FOREIGN PATENT DOCUMENTS

EP   0 369 998 A2   5/1990

OTHER PUBLICATIONS

Patent Abstracts of Japan vol. 002, No. 144 (c–029), Nov. 30, 1978.
Patent Abstracts of Japan vol. 007, No. 201 (c–184), Sep. 6, 1983.
Patent Abstracts of Japan vol. 096, No. 001, Jan. 31., 1996.

* cited by examiner

*Primary Examiner*—Jerry A. Lorengo
(74) *Attorney, Agent, or Firm*—Marshall, Gerstein & Borun

(57) ABSTRACT

Method and apparatus for coating the surface of an object, especially the surface of a car bumper (1) with a plastic film (2). During and/or after application of the plastic film to the surface, the coating is irradiated with infra-red radiation in order to heat at least parts of the coating and/or optionally residual moisture between the surface and the plastic film (2). This enables slight inequalities of the plastic film to be compensated, the adhesive coating is distributed in a homogeneous manner and the optionally residual moisture is collected in the form of bubbles following infrared radiation. Defects or irregularities in the coating can thus be identified during or shortly afterwards.

15 Claims, 1 Drawing Sheet

METHOD AND DEVICE FOR COATING A SURFACE WITH A PLASTIC FILM

BACKGROUND OF THE INVENTION

The invention relates to the process of coating a surface with a thin sheet of plastic, in particular the surface of an automobile bumper. In particular, during such a surface coating process, the surface and/or the plastic sheet is moistened so that after the plastic sheet has been applied, the surface in at least some places is separated from the plastic sheet by a film of moisture, which is subsequently at least partially removed by a squeegee. The invention further relates to quality assurance during the implementation of a method for coating a surface with a thin plastic sheet, in particular the surface of an automobile bumper.

For various reasons, it is a common current practice to coat the surfaces of objects with thin sheets of plastic. For example, such plastic sheets protect vulnerable surfaces from becoming scratched and from the action of chemicals, and they can also create colour impressions by interference effects or can make the surface more shiny. In the automobile industry, for instance, it is customary to provide cars with bumpers, the colour of which is coordinated with the colour of the body paint. The bumpers are made of a plastic material of the desired colour which, however, often is relatively soft and flexible, so that the surface readily becomes scratched as a result of everyday wear and tear. Furthermore, the scratches on a smooth, preferably shiny, lacquer-like plastic surface are considerably more clearly visible than they would be on matte, roughly textured surfaces.

A known means of coating a surface with a thin sheet of plastic, in particular the surface of a car bumper, is to moisten the surface and/or the plastic sheet so that after the sheet has been applied, the surface is separated from the sheet, at least in places, by a film of moisture. The liquid that forms the film of moisture can, in particular, be a rinsing solution. The moisture film permits the plastic sheet to be positioned or repositioned on the surface in exactly the desired manner. After the plastic sheet has been positioned at the correct place or in the correct region on the surface, the moisture film is at least partially, preferably almost completely, removed by means of a squeegee.

Some of the moisture is usually bound to the surface and/or to the plastic sheet. Another portion can enter into combination with an adhesive that has likewise been disposed between the plastic sheet and the surface. In many cases the moisture actually serves to activate the adhesive, so that an effective and permanent adhesion is achieved.

However, if most of the superfluous moisture is not squeezed out, the result can be distinctly visible irregularities in the coating. In particular, over a period of several hours moisture contents that had been bound in one of the ways described above, or had been relatively uniformly distributed over the surface, can collect and form moisture-filled blisters. This presents a major problem for automobile manufacture, particularly in the case of the currently customary just-in-time delivery of fittings. In some circumstances large numbers of, for example, a car bumper must be produced and delivered in a relatively short time, in which case any defects in the coating do not become apparent until after the bumpers have been delivered or even mounted on the cars.

Another problem is presented by irregularities in the plastic sheet and/or in the layer of adhesive that has been applied to the sheet or to the surface before the coating process is begun. In particular, the thickness of the plastic sheet or the consistency of the plastic material may be nonuniform. Such irregularities in the plastic sheet and/or an adhesive layer often do not become visible until the plastic sheet has been applied to the surface of the object to be coated. The reason is, in particular, that the plastic sheet in many cases is transparent and defects are detectable only when irregularities are seen in the light reflected or refracted by the coated surface. Furthermore, a nonuniform distribution of the adhesive can be produced in particular by the process of removing the moisture film between the plastic sheet and the surface with a squeegee.

SUMMARY OF THE INVENTION

An object of the present invention is to disclose a method of coating a surface with a thin plastic sheet, in particular the surface of an automobile bumper of the kind described at the outset, by means of which the smallest possible number of defective products are delivered. In this method any defects that occur are detected as quickly as possible, and wherever possible slight irregularities in the coating are eliminated. Another object of the present invention is to disclose an apparatus for coating a surface with a thin sheet of plastic, by means of which the above requirements can be fulfilled.

Furthermore, it is an object of the present invention to disclose a means of employing equipment in such a way as to satisfy the above requirements.

An essential idea in the invention presented here is that the coating of the surface is irradiated with infrared radiation during and/or after removal of the moisture film with a squeegee, in order to warm up at least portions of the coating and/or, where appropriate, residual moisture remaining between the surface and the plastic sheet.

When such residual moisture is present, the warming accelerates processes that in the absence of warming would take a longer time to complete or would not even be initiated until a later, unpredictable time when, for example, the coating is exposed to extreme external influences such as a high ambient temperature or intense solar irradiation. Hence in a short time it can be determined whether the coating satisfies predetermined quality criteria.

The infrared radiation can be absorbed by the plastic sheet itself and/or by the residual moisture and/or by an adhesive layer, if one is present. Preferably, however, the greatest proportion of the incident energy is absorbed directly in the region between the surface of the object to be coated and the plastic sheet. In particular when the period of irradiation is brief, with high radiation flux densities, the warming is brought about at the desired place with no appreciable heating of the plastic sheet or the object to be coated. Usually such plastic sheets are temperature-sensitive, being deformed thermoplastically at temperatures above a damage-level. In the preferred embodiment described here, therefore, damage to the plastic sheet and/or the object to be coated can be avoided with high reliability.

Especially preferred is a further development in which a largely continuous radiation spectrum is employed, the spectral radiation density maximum of which lies in a wavelength range beyond the visible region, up to a wavelength of 1.4 $\mu$m. This region is called the near infrared.

In a preferred further development of the method, any residual moisture that is present is affected by the infrared radiation in such a way that it collects to form blisters. Thus only a short time after, or even during the irradiation defects in the application of the plastic sheet or in the removal of the moisture film can be detected. These products can be rejected and/or coated anew. In distinction to the known method described above, the present method allows quality control to be carried out immediately after the actual coating process. A later quality control, e.g. in an automobile production line, can therefore be eliminated, with a saving of work time and personnel costs.

Often an adhesive layer disposed between the surface and the plastic sheet is used to attach the plastic sheet. Preferably in such cases the coating is irradiated in such a way that the adhesive layer is warmed by the irradiation and spreads out uniformly. The result is good adhesion of the coating everywhere, with no visually discernible irregularities caused by the adhesive layer.

When it is likely that there will be nonuniformities in the plastic sheet, such as an uneven thickness of the sheet or a nonuniform structure of the plastic material, the irradiation evens them out, at least approximately, in particular if they are only slight irregularities. In this case an appreciable absorption of the infrared radiation does take place, especially in the plastic sheet, so that a homogenization, for instance a uniform polymerization, is brought about. However, irregularities can be restricted to the surface of the plastic sheet, so that it is preferable for most of the radiation energy to be absorbed in this region, producing a smoothing of the sheet surface.

When a car bumper is to be coated with a piece of plastic sheet that extends approximately over the entire width and length of the bumper, the coating sheet is preferably irradiated for a total time of less than 20 s, in particular less than 10 s, in which process the infrared radiation is preferably emitted by a halogen bulb, the incandescent filament of which has a surface temperature of more than 2500 K.

The apparatus in accordance with the invention for coating a surface with a thin plastic sheet, in particular the surface of a car bumper, comprises a radiation source to generate infrared radiation and a reflector to increase the flux density of the radiation emitted by the source and incident on the coating.

The infrared radiation heats at least parts of the coating applied to the surface, and/or accessory materials used during coating such as liquids or substances added thereto. In particular, the method described above can be implemented in at least one of its variants.

In particular when the process of coating the surface of a car bumper is carried out at a manufacturing station, the apparatus preferably comprises a holding device to hold the object to be coated and a displacement device to change the position of a beam emitted from the radiation source and directed onto a particular, limited part of the coating. By means of the displacement device the radiation beam or the radiation source can be shifted along the surface of the object to be coated, in order to irradiate other parts of the coating as well. The displacement device is advantageously driven by a motor, which in particular is operated according to predetermined control parameters, so that the movement of the incident beam occurs according to a specific program.

In a further development of the apparatus the displacement device comprises a guide element, in particular a rail, along which the radiation source can be shifted. Preferably the guide element is bent to conform to the shape of the object to be coated, so that while the radiation source is displaced, its distance from the surface of the object to be coated is kept constant. In this case, the control program is advantageously such that the radiation source is displaced along the guide element with constant velocity.

An advantage of the apparatus in accordance with the invention is that the object to be coated is not moved as it would be on a production line, but instead is kept stationary, so that a precise positioning of the plastic sheet on the surface to be coated can be carried out while the object is at rest. At a specified time the displacement device can be activated, while the object is still being held by the holding device.

In a preferred embodiment of the apparatus the radiation source comprises at least one halogen bulb, which in particular can be operated at surface temperatures of more than 2500 K. To generate special radiation spectra radiation filters, for example a glass pane with the desired optical properties, are disposed between the radiation source and the coating to be irradiated. The sites at which the incandescent filament of the halogen bulb are attached are preferably cooled by a ducted air current. By this means the working life of the halogen bulb can be distinctly increased. It is also preferable for the reflector to be kept at or below a predetermined temperature by liquid cooling, to keep the reflection properties of the reflector constant and to ensure that the reflector is exposed to as little thermal stress as possible.

In a particularly preferred embodiment the apparatus comprises a control device to regulate the coating temperature, including a pyrometer aimed at the coating to measure the temperature thereof. The control device in particular prevents the plastic sheet from becoming so warm as to be damaged.

An additional idea in accordance with the invention provides that during the implementation of a method for coating a surface with a thin sheet of plastic, in particular according to an embodiment of the method described above, an infrared bulb is used for quality control, such that the coating is irradiated with infrared radiation from the infrared bulb in order to render visible irregularities in the coating and/or to eliminate them, at least approximately. Preferably the infrared bulb is a halogen bulb. In a particular embodiment the infrared bulb is a tubular radiator with an elongated incandescent filament extending linearly within a tube, in particular a quartz-glass tube, that is transparent to the radiation. The infrared bulb is advantageously combined with a reflector that extends in the long direction of the tube and curves around the back side thereof, so that it has the form of a channel in cross section, with the result that the radiation emitted from the front side of the tube is enhanced by reflected radiation. Thus an undesired emission of radiation in the direction of the back side is avoided, and the efficacy of the arrangement is increased. Furthermore, the reflector can serve to provide a particular radiation flux density distribution over the irradiated region of the coating, in particular to achieve a constant radiation flux density distribution.

BRIEF DESCRIPTION OF THE DRAWINGS

Exemplary embodiments of the present invention will now be described with reference to the drawing. However, the invention is not restricted to these exemplary embodiments. The individual figures in the drawing are as follows.

DETAILED DESCRIPTION

Figure 1:
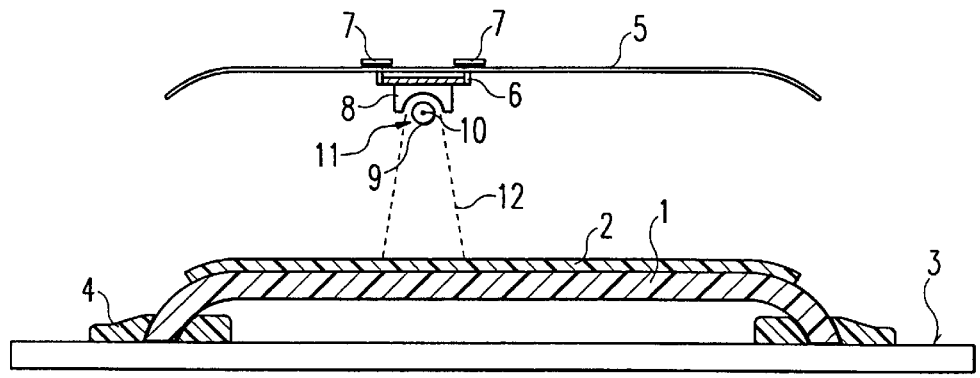
FIG. 1 is an exemplary embodiment of the apparatus in accordance with the invention.

FIG. 1 shows an embodiment of the apparatus in accordance with the invention that comprises a supporting surface 3 onto which a car bumper 1 is placed. The car bumper 1 is held by retention clamps 4 that are fixed in position on the supporting surface 3. In this case the bumper 1 is part of a safety bumper arrangement to be mounted on the rear end of an automobile in the region of the door to the luggage compartment. The bumper 1 is made of a plastic material that is colour-coordinated with the paint on the body of the car. In particular in order to prevent scratching of the bumper 1, by means of the apparatus shown in FIG. 1 a thin sheet of polyethylene (PE) is applied to the upper surface of the bumper 1. In FIG. 1 the PE sheet 2 is drawn thicker than it actually is.

The apparatus shown here comprises a rail 5, along which a halogen bulb 11 can be shifted. The halogen bulb 11, as can be seen in the cross-sectional drawing, is surrounded on its back side by a channel-shaped reflector 8, which enhances the radiation emitted from the front side by adding reflected radiation. The reflector 8 is attached to a bulb holder 6, which in turn is connected to two slides 7 that are guided by the rail 5 and permit the halogen bulb 11 to be displaced.

The quartz-glass tube and the incandescent filament 10 of the halogen bulb 11 extend perpendicular to the plane of FIG. 1 over a distance corresponding approximately to the width of the PE sheet 2. Because of the combination of the halogen bulb 11 with the reflector 8, a beam 12 of radiation that diverges slightly to the sides is incident on a region covering part of the coating applied to the bumper 1. By shifting the arrangement along the rail 5, the entire coating can be uniformly irradiated. The ends of the rail 5 are bent to correspond to the shape of the bumper 1, so that the end regions of the PE sheet 2 can be irradiated from the same distance as the middle section of the PE sheet 2.

The halogen bulb 11 is preferably operated in such a way that the surface temperature of the incandescent filament 10 amounts to about 3000 K. The maximum of the spectral radiation flux density distribution is therefore at approximately 1 μm wavelength, i.e. in the near infrared.

Figure 2:
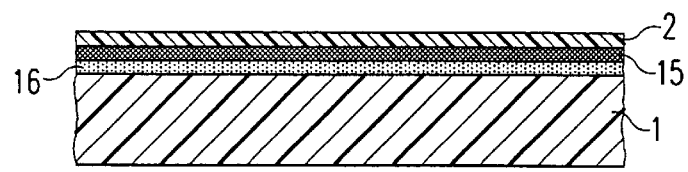
FIG. 2 shows an example of the structure of a coating before a film of moisture between the plastic sheet and the surface to be coated has been removed with a squeegee.
Figure 3:
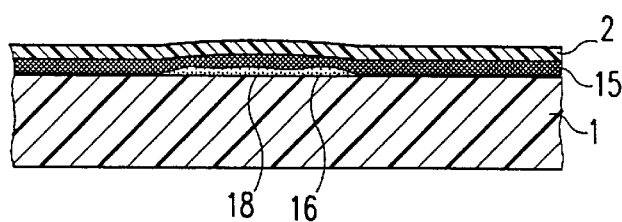
FIG. 3 shows the structure of the coating according to FIG. 2 after treatment with the squeegee and FIG. 4 shows the structure of the coating according to FIG. 3 immediately after infrared irradiation.
Figure 4:
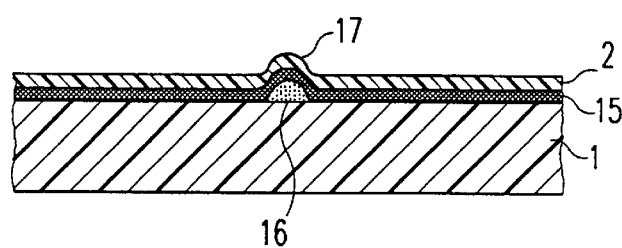

With reference to FIGS. 2–4 an exemplary embodiment of the method in accordance with the invention will now be described, for which in particular the apparatus according to FIG. 1 can be used. The figures show cross sections through a particular restricted part of the bumper 1 according to FIG. 1 at various stages of the process.

First the surface of the bumper 1 that is to be coated is wet with an aqueous rinsing solution 16. Then the PE sheet 2, the under surface of which has previously been provided with an adhesive layer 15, is set onto the wet surface. The resulting state is illustrated in FIG. 2. It can also happen, in contrast to the situation shown here, or it can even be necessary in order to obtain adequate adhesion, for the adhesive layer 15 to take up moisture, i.e. the rinsing solution, in order to enable the PE sheet to be shifted into precisely the desired position in a simple manner. However, it is advantageous if an excess of rinsing solution 16 is present, because this prevents or delays the development of the attachment action of the adhesive and represents a lubricating film with a low coefficient of friction. After the PE sheet 2 has been put into place, the rinsing solution is squeezed out, at least to a great extent, by hand or with a suitable tool. As a result the adhesive 15 develops its adhesive action and fixes the PE sheet 2 to the surface of the car bumper 1. The condition shown in FIG. 3 is thereby achieved, namely that despite efforts to squeeze out the liquid, in part of the coated region superfluous rinsing solution 16 still remains on the surface of the bumper 1, as residual moisture 18. The residual moisture 18 is present in a thin layer, because it is bound to the surface of the car bumper and/or to the adhesive 15 or the lower surface of the PE sheet 2. Furthermore, the adhesive 15 forms a layer of nonuniform thickness, in particular in the region of the residual moisture 18.

Now if one were to wait for a few hours without carrying out any other procedural steps, the adhesive 15 would become completely detached from its binding to the fluid, and in some circumstances would release additional bound particles of the rinsing solution, so that the residual moisture 18 would gradually accumulate in a confined space and be clearly visible from outside as a blister 17, as shown in FIG. 4. Such a coating does not meet the customary quality criteria, so that the bumper 1 must be rejected before being mounted, or if it has already been mounted on an automobile it would have to be removed and replaced or coated again.

Hence in accordance with the invention, for quality assurance the coating of the bumper 1 is irradiated with infrared radiation during and/or after the moisture has been squeezed out, so that firstly the adhesive 15 becomes distributed in a uniform thickness over the surface of the bumper 1 (with the exception of the region where residual moisture 18 is present) and, secondly, the residual moisture 18 collects to form a blister 17. The term "blister" is used here for any clearly visible elevation of the plastic sheet that is the cause of an accumulation of liquid; in particular it is also possible for elongated, wavelike blisters to form. Thus already during or shortly after the irradiation it is detectable whether the coating meets the quality criteria. Furthermore, in case no superfluous residual moisture is made visible, it follows that the adhesive layer is uniformly thick everywhere. In addition, such slight nonuniformities of the plastic sheet as may be present, detectable for example as streaks or cloudlike structures, can be evened out by the warming.

LIST OF REFERENCE NUMERALS

1 Automobile bumper
2 PE sheet
3 Supporting surface
4 Retaining clamps
5 Rail
6 Bulb holder
7 Slide
8 Reflector
9 Quartz-glass tube
10 Incandescent filament
11 Halogen bulb
12 Radiation beam
15 Adhesive
16 Rinsing solution
17 Blister
18 Residual moisture

What is claimed is:

1. A method of coating a surface with a plastic sheet comprising:
   moistening the surface and/or plastic sheet;
   applying the plastic sheet to the surface so that at least a portion of the surface is separated from the plastic sheet by a film of moisture, the plastic sheet and film of moisture defining a coating;
   removing at least a portion of the film of moisture from between the plastic sheet and surface by squeezing, so that at least one area of residual moisture remains between the surface and the plastic sheet;

irradiating the coating with infrared radiation from a tubular infrared bulb extending over a distance corresponding approximately to a width of the plastic sheet, the irradiating step occurring during and/or after the removing step so that at least a portion of the coating and/or the at least one area of residual moisture is heated.

2. A method according to claim 1, in which the at least one area of residual moisture forms a blister during the irradiating step.

3. A method according to claim 1, in which the coating further comprises an adhesive layer disposed between the surface and the plastic sheet, and in which the adhesive layer is heated during the irradiating step so that the adhesive layer spreads uniformly over the surface.

4. A method according to claim 1, in which the plastic sheet includes nonuniformities, and in which the nonuniformities are at least partially smoothed during the irradiation step.

5. A method according to claim 1, in which the infrared radiation has a spectral radiation flux density maximum in the near infrared.

6. A method according to claim 1, in which the coating is irradiated for a total of less than 20 seconds.

7. Apparatus for processing a surface having a coating of at least a plastic sheet, the apparatus comprising:
a holding device sized to hold an object having the surface to be coated;
a source of infrared radiation including a tubular bulb extending over a distance corresponding approximately to a width of the plastic sheet, the bulb positioned to heat at least a portion of the coating and/or accessory materials used in the coating process, the tubular bulb having a front side facing toward the surface and a back side facing away from the surface;
a reflector positioned adjacent the back side of the tubular bulb to increase a flux density of a radiation beam emitted by the tubular bulb and incident on the coating; and
a displacement device attached to the source of infrared radiation for shifting the radiation beam along the surface to irradiate substantially an entire area of the coating.

8. Apparatus according to claim 7, wherein the displacement device comprises a guide element along which the source of infrared radiation is shifted.

9. Apparatus according to claim 8, wherein the guide element is bent to correspond to a shape of the object, so that a uniform distance is maintained between the source of infrared radiation and the coating as the source of infrared radiation is shifted along the guide element.

10. Apparatus according to claim 7, wherein the radiation source comprises at least one halogen bulb operable at a surface temperature of at least 2500 K.

11. Apparatus according to claim 7, further comprising a pyrometer for measuring a coating temperature and a control for regulating the coating temperature.

12. A method of performing quality assurance on a coating attached to a surface, the coating including a plastic sheet, the method comprising:
securing the surface and attached coating with a holding device;
generating infrared radiation from a tubular bulb having a front side facing toward the surface and a back side facing away from the surface;
reflecting infrared radiation emitted from the rear side of the bulb toward the surface to increase a flux density of the infrared radiation emitted by the tubular bulb and incident on the coating; and
shifting a radiation beam directed from the tubular bulb along the surface and coating to irradiate substantially an entire area of the coating;
wherein the infrared radiation incident on the coating increases visual detection of irregularities in the coating and/or reduces the irregularities in the coating.

13. A method according to claim 12, wherein the infrared bulb comprises a halogen bulb.

14. A method according to claim 12, wherein the tubular bulb comprises an incandescent filament extending linearly within a quartz-glass tube.

15. A method according to claim 14, wherein the infrared radiation emitted from the back side of the tubular bulb is reflected by a reflector positioned along a back side of the tube, the reflector having a channel-shaped cross-section open toward the surface.

* * * * *